US010548937B2

(12) United States Patent
Bijno et al.

(10) Patent No.: US 10,548,937 B2
(45) Date of Patent: Feb. 4, 2020

(54) COMPOSITION FOR THE TREATMENT OF ARTHROPATHIES AND OSTEOARTHRITIS

(71) Applicant: Kolinpharma S.p.A., Milan (IT)

(72) Inventors: Domenico Bijno, Milan (IT); Carmine Di Vincenzo, Milan (IT); Emanuele Lusenti, Milan (IT); Alberto Martina, Milan (IT); Ritapaola Petrelli, Milan (IT)

(73) Assignee: Kolinpharma S.p.A., Milan (IT)

( * ) Notice: Subject to any disclaimer, the term of this patent is extended or adjusted under 35 U.S.C. 154(b) by 0 days.

(21) Appl. No.: 15/503,088

(22) PCT Filed: Aug. 18, 2015

(86) PCT No.: PCT/IB2015/056275
§ 371 (c)(1),
(2) Date: Feb. 10, 2017

(87) PCT Pub. No.: WO2016/027230
PCT Pub. Date: Feb. 25, 2016

(65) Prior Publication Data
US 2017/0239308 A1    Aug. 24, 2017

(30) Foreign Application Priority Data

Aug. 20, 2014 (IT) .............................. TO2014A0674

(51) Int. Cl.
| | |
|---|---|
| A61K 36/00 | (2006.01) |
| A61K 36/54 | (2006.01) |
| A61K 31/10 | (2006.01) |
| A61K 31/375 | (2006.01) |
| A61K 31/7076 | (2006.01) |
| A23L 33/11 | (2016.01) |
| A23L 33/16 | (2016.01) |
| A23L 33/15 | (2016.01) |
| A61K 9/00 | (2006.01) |
| A61K 31/198 | (2006.01) |
| A61K 36/48 | (2006.01) |

(52) U.S. Cl.
CPC .............. *A61K 36/54* (2013.01); *A23L 33/11* (2016.08); *A23L 33/15* (2016.08); *A23L 33/16* (2016.08); *A61K 9/009* (2013.01); *A61K 9/0053* (2013.01); *A61K 31/10* (2013.01); *A61K 31/198* (2013.01); *A61K 31/375* (2013.01); *A61K 31/7076* (2013.01); *A61K 36/48* (2013.01); *A23V 2002/00* (2013.01)

(58) Field of Classification Search
None
See application file for complete search history.

(56) References Cited

U.S. PATENT DOCUMENTS

2007/0141181 A1* 6/2007 Henderson ............. A61K 31/56
424/735
2012/0141387 A1    6/2012 Msika et al.

OTHER PUBLICATIONS

Smith, Vitamin C deficiency is an under-diagnosed contributor to degenerative disc disease in the elderly. Medical hypotheses, (Apr. 2010) vol. 74, No. 4, pp. 695-697.*
"Amino acid studies", 2014, http://aminoacidstudies.org/osteoarthritis/, Accessed Apr. 13, 2015.
"Arthro NRx™ Eases Osteoarthritic Symptoms", Bioclinic Naturals, 2014, http://bioclinicnaturals.com/ca/en/products/Detail/6015/arthro-nrx, Accessed Nov. 12, 2015.
Borderie et al., "Inhibition of the nitrosothiol production of cultured osteoarthritic chondrocytes by rhein, cortisol and diclofenac", Journal of the OsteoArthritis Research Society International, 2001, vol. 9, pp. 1-6.
"DJD Factors", XYMOGEN Exclusive Professional Formulas, 2013, http://www.xymogen.com, Accessed Nov. 12, 2015.
"Flexi-Smart 300mg", Online Dietary and Nutritional Supplements, 2013, http://www.super-smart eu/en-Joints--Fiexi-Smart-30-mg--0583, Accessed Nov. 12, 2015.
Lopez, "Nutritional Interventions to Prevent and Treat Osteoarthritis. Part II: Focus on Micronutrients and Supportive Nutraceuticals", Physical Medicine and Rehabilitation: The Journal of Injury, Function, and Rehabilitation, 2012, vol. 4, pp. s155-s168.
Marcu et al., "NF-kB Signaling: Multiple angles to target OA", Curr Drug Targets, 2010, vol. 11, No. 5, pp. 599-613.
Nakamura et al., "Effects of celecoxib on human chondrocytes-enhanced production of chemokines", Clinical and Experimental Rheumatology, 2007, vol. 25, pp. 11-16.
Noursadeghi et al., "Quantitative imaging assay for NF-kB nuclear translocation in primary human macrophages", Journal of Immunological Methods, 2008, vol. 329, pp. 194-200.
Pelletier et al., "Osteoarthritis, an Inflammatory Diesease", Arthritis & Rheumatism, 2001, vol. 44, No. 6, pp. 1237-1247.
"S-Adenosyl L-Methionine Tablet", 2014, http://dmpharma.co.in/t19.html, Accessed Apr. 13, 2015.
Shakibaei et al., "Suppression of NF-kB activation of Curcumin leads to inhibition of expression of cyclo-oxygenase-2 and matrix metalloproteinase-9 in human articular chondrocytes: Implications for the treatment of osteoarthritis", Biochemical Pharmacology, 2007, vol. 73, pp. 1434-1445.
Song et al., "S-adenosylmethionine (SAMe) modulates interleukin-10 and interleukin-6, but not TNF, production via the adenosine (A2) receptor", Biochimica Et Biophysica ACTA, 2005, vol. 1743, pp. 205-213.

(Continued)

*Primary Examiner* — Qiuwen Mi
(74) *Attorney, Agent, or Firm* — MacMillan, Sobanski & Todd, LLC (57) ABSTRACT

A pharmaceutical composition or dietary supplement with antagonist activity on the degradation and degeneration of cartilage tissue, anti-inflammatory and analgesic activity is described, which is effective in the treatment of arthropathies and osteoarthritis, comprising, as active ingredients, a combination of methylsulfonylmethane, unsaponifiables of avocado and/or soybean, and S-adenosyl-L-methionine.

14 Claims, 5 Drawing Sheets

(56) References Cited

OTHER PUBLICATIONS

Wu et al., "Insights on Biology and Pathology of HIF-1α/-2α, TGFβ/BMP, Wnt/β-Catenin, and NF-κB Pathways in Dsteoarthritis", Current Pharmaceutical Design, 2012, vol. 18, pp. 3293-3312.
PCT Written Opinion and International Search Report, Application No. PCT/IB2015/056275, dated Nov. 20, 2015.

* cited by examiner

COMPOSITION FOR THE TREATMENT OF ARTHROPATHIES AND OSTEOARTHRITIS

This is a national stage application filed under 35 U.S.C. § 371 of international application PCT/IB2015/056275, filed under the authority of the Patent Cooperation Treaty on Aug. 18, 2015, published; which claims the benefit of Patent Application No. TO2014A000674, filed on Aug. 20, 2014. The entire disclosures of all the aforementioned applications are expressly incorporated herein by reference for all purposes.

The invention relates to a composition with antagonist activity on the degradation and degeneration of cartilage tissue, anti-inflammatory and analgesic activity, for use as a dietary supplement or medicament in the treatment of arthropathies and osteoarthritis.

The subject of the invention is a formulation for oral administration, which is free of particular contraindications both as regards the individuals to whom it may be administered and as regards the administered amounts, and which has an antagonist effect on the degradation and degeneration of cartilage tissue, and an anti-inflammatory and analgesic effect.

The composition that is the subject of the present invention is characterized in that it comprises, as active ingredients, a combination of methylsulfonylmethane, unsaponifiables of avocado and/or soybean and S-adenosyl-L-methionine.

Further characteristics of the composition of the invention and of its use are defined in the attached claims, which form an integral part of the present description.

Methylsulfonylmethane (or MSM) is a biologically active form of sulfur, which plays a fundamental role in maintaining the integrity of the joints and the elasticity of connective tissue. Sulfur is present in high concentrations in the joints and its supplementation is useful for promoting the production of glycosaminoglycans and other components of cartilage tissue.

Cartilage is a highly specialized tissue that covers the surface of bone extremities of all joints and allows fluid, frictionless movement of the joints, in addition to providing exceptional resistance to mechanical stresses.

In this context, sulfur plays a determining structural role, by establishing disulfide bridges between collagen fibres. A sulfur deficiency may lead to the breaking of the disulfide bridges present in cartilage tissue.

Methylsulfonylmethane exerts powerful anti-inflammatory action by inhibiting the expression of interleukins (IL-6 and IL-8), which are inflammation mediators in the chondrocytes.

The avocado and/or soybean unsaponifiables (ASU) is obtained by fractionation of the respective oils and is characterized by the presence of plant sterols, such as beta-sitosterol, beta-sitosterol glucoside, sigmasterol and capesterol. This substance inhibits the activity of two enzymes responsible for cartilage degradation, metalloproteases and NO synthase.

ASU is capable of reducing the production of MMP-3 and of stimulating the synthesis of TIMP-1 (tissue inhibitor of metalloproteases), proving to be effective in increasing the production of aggrecan in arthrotic chondrocytes.

According to a preferred embodiment, the composition that is the subject of the present invention comprises unsaponifiables of avocado and soybean with a phytosterol titre of at least 30%.

S-Adenosyl-L-methionine (SAMe) is a coenzyme involved in transferring the methyl group bonded to the chemically reactive sulfur to a second molecule, making SAMe a catalyst of many enzymatic reactions. SAMe is a methyl group donor and is involved in the biosynthesis of many mood-related hormones and neurotransmitters, such as serotonin and dopamine, and even at a dose of 200 mg, it is effective in reducing the symptoms of depression, as much as tricyclic antidepressant drugs. It does not show any side effects and is well tolerated by patients. SAMe is thus useful in raising the pain threshold.

According to a preferred embodiment, S-adenosyl-L-methionine is present in the composition that is the subject of the present invention in the form of pharmaceutically acceptable salts, for instance S-adenosyl-L-methionine sulfate p-toluenesulfonate.

The combination of the above-mentioned active principles in the composition according to the invention is particularly advantageous since they develop a synergistic effect.

According to a preferred aspect of the present invention, the compositions under consideration may contain additional components, with curative or complementary action, or else may be useful for the purposes of the proposed invention. Examples of such additional components are vitamin C, copper and manganese.

Vitamin C is a water-soluble vitamin, which is a cofactor of the important reactions for collagen maturation, such as the hydroxylation of lysine and proline performed by proline hydroxylase and lysine hydroxylase. Vitamin C contributes towards the formation of collagen for the normal function of cartilages.

Copper, which is present in the composition that is the subject of the invention preferably as copper bisglycinate chelate, is an essential element for man. In tissues, it acts especially as a cofactor of many enzymes, which are in turn involved in various physiological functions. Copper contributes towards maintaining the structure of connective tissues and up-regulates collagen anabolism by the human articular chondrocytes.

Manganese is an essential mineral, which is present in the human body at between 12 and 20 mg. Many classes of enzymes contain one or more manganese atoms as cofactors.

Manganese is a cofactor for superoxide dismutase (SOD), an important cellular antioxidant. Superoxide dismutase (SOD), which contains an Mn atom in its catalytic site, promotes mitochondrial detoxification.

Manganese supplementation induces cartilage cells to synthesise more SOD, making the detoxification of the area concerned by the inflammatory process more effective.

It is also thought that an increase in the biosynthesis of glycosaminoglycans (GAG) is dependent on the intake of manganese with the diet.

According to a preferred embodiment, manganese is present in the composition that is the subject of the present invention in the form of manganese bisglycinate.

The compositions of the invention may be formulated in any form suitable for oral administration, for example as soft or hard gelatin capsules, tablets, effervescent or chewable tablets, granules or powders in a sachet, controlled-release solid forms, chewing gums and the like.

The compositions of the present invention may be formulated in a manner suitable for oral administration and will be prepared according to conventional methods that are well known in the pharmaceutical field, such as those described in "Remington's Pharmaceutical Handbook", Mack Publishing Co., N.Y., USA, using excipients, diluents, fillers and anticaking agents that are acceptable for the final use thereof.

The experimental section that follows describes studies that were performed relating to the biological effects of the composition of the invention. In the description of the studies performed, reference is made to the attached figures, in which.

A particularly preferred formulation of the composition of the invention, used in the experimental studies, is also given hereinbelow. In addition to the indicated active principles, the formulation may also comprise suitable excipients, colorants, flavourings, granulating agents, acidifying agents, emulsifiers, sweeteners and anticaking agents.

FORMULATION EXAMPLE—5 G SACHET

| INGREDIENTS | mg/sachet |
| --- | --- |
| Methylsulfonylmethane | 2500.00 |
| Vitamin C | 250.00 |
| Unsaponifiables of avocado and soybean with a phytosterol titre of 30% | 150.00 |
| S-Adenosyl-L-methionine sulfate p-toluenesulfonate | 100.00 |
| Manganese bisglycinate | 62.50 |
| Copper bisglycinate | 9.00 |

The recommended dose is one or two sachets per day.

Experimental Section

Rationale

The composition of the above preparative example was used in the experimental study described hereinbelow.

The pathological target of this composition is arthropathies of primary and secondary origin. Pro-inflammatory cytokines, such as interleukin 1β(IL-1β) and tumour necrosis factor α(TNF-α), play a key role in the pathogenesis of osteoarthritis. Interleukin 1β(IL-1β) and tumour necrosis factor α(TNF-α) induce the production of IL-8 and IL-6, leukaemia inhibitory factor (LIF) and prostaglandin E2 (PGE2). In cartilage, these cytokines are produced by synovial cells and by chondrocytes. One of the therapeutic targets in the treatment of osteoarthritis is inhibition of the activity of the pro-inflammatory cytokines IL-1β and TNF-α(Pelletier J-P, 2001, Arthritis & Rheumatism).

Object of the Study

In the experimental study performed, the anti-inflammatory activity of the test composition was analysed, in primary human chondrocytes cell cultures following stimulation with IL-1β. The capacity of the composition to inhibit transduction of the signal, which, from the extracellular stimulus (IL-1β), leads to the production of the cytokines TNF-α, IL-8 and IL-6 and to the activation and nuclear translocation of nuclear factor Kappa B (NF-kB), was evaluated quantitatively by means of ELISA tests (cytokines; Test 1a) and immunolabelling and analysis with a confocal microscope (translocation of NF-kB; Test 1b). NF-kB is a translocation factor which plays a ubiquitous role in the inflammatory process. Once activated, NF-kB is capable of translocating from the cytoplasm to the nucleus, binding specific DNA sequences and modulating the expression of numerous cytokines and chemokines, adhesion molecules, inflammatory mediators and various enzymes capable of degrading the extracellular matrix (Wu L. et al., Curr. Pharm. Des. 2012; 18(22): 3293-312; Marcu K. B., et al., Curr. Drug Targets, 2010 May; 11(5): 599-613). NF-kB thus plays a central role in the pro-inflammatory and stress-related response of chondrocytes to both intracellular and extracellular attack.

Materials and Methods

Dolasix

As indicated in the preparative example, the test composition (indicated hereinabove as DOLASIX) contains methylsulfonylmethane, S-adenosylmethionine, unsaponifiable materials of soybean and avocado, copper, manganese and vitamin C.

The whole compound was insoluble in water, methanol, xylene, acetone and DMSO. The insolubility was due to the presence of the unsaponifiable materials of soybean and avocado, which, even individually, it was not possible to dissolve completely. Stock solutions were thus prepared (prepared at a higher concentration than the final concentration with which the cells were incubated) of each component, which were then mixed together to reproduce DOLASIX. The concentration of S-adenosylmethionine (SAMe) 500 µM was taken as reference (Song Z. et al., Biochimica et Biophysica Acta 1743 (2005) 205-213). Based on the concentration of SAMe, the other components were added to form the final composition, keeping the same relative amounts present in DOLASIX, as illustrated in Table 1.

TABLE 1

| Component | [final] in mM | solvent |
| --- | --- | --- |
| SAMe | 0.5 | water |
| Methylsulfonylmethane | 9.30 | water |
| Unsaponifiable materials of soybean and avocado | 0.1 mg/ml | water |
| Vitamin C | 0.95 | water |
| Copper bisglycinate | 0.002 | water |
| Manganese bisglycinate | 4.35 | water |

The positive controls with which the effects produced by DOLASIX in the cell tests are compared were: celecoxib 10 µM (Nakamura H. et al., Clinical and Experimental Rheumatology (2007) 25: 11-16) and diclofenac 100 µM (Borderie D. et al., OsteoArthritis and Cartilage (2001) 9: 1-6) for the anti-inflammatory effect (Tests 1a and 1b).

Cells

Human chondrocytes (Lonza, cat. N. CC-2550) derived from knee tissue were cultured in Chondrocyte Growth Medium (Lonza, cat. N. CC-3216) prepared according to the manufacturer's instructions with the addition of R3-insulin-like growth factor-1 [R3-IGF-1], human recombinant fibroblast growth factor beta [hrFGF-β], transferrin, insulin, foetal bovine serum [FBS] and gentamicin/amphotericin-B [GA]. The cells were maintained in an incubator at 37° C. and 5% $CO_2$ and seeded every 3-4 days at a density of about $1 \times 10^4$ cells/$cm^2$.

For all the tests performed, the cells were seeded in the evening in 24-well or 96-well multiwell plates according to the test, and incubated with various concentrations of DOLASIX, of its vehicle, of the positive controls in whole medium in the presence or absence of IL-1β as inflammatory stimulus at a concentration of 10 ng/ml (Shakibaei M. et al., Biochemical Pharmacology (2007) 73: 1434-1445). After about 16-20 hours of incubation, the cells were processed for the various tests.

MTT Test (Test 0)

To check that the incubation with DOLASIX at the concentrations and for the times chosen was not toxic to the cells, the MTT test (Test 0) was performed. This colorimetric test is based on the transformation of the tetrazolium salt MTT (yellow) into formazan (violet), by the succinate-tetrazolium reductase system, which belongs to the mitochondrial respiratory chain and is active only in metabolically active cells. Briefly, the cells grown in a 96-well multi-well plate were incubated with MTT solution for 4 hours. An insoluble colorant forms during this period, which, after dissolving by adding dissolution solution to the samples (10% SDS in 10 mM HCl) and after incubating overnight in an incubator, may be quantified by reading the absorbance of the samples at 595 nm (using 750 nm as reference wavelength). The measured absorbance correlates directly with the number of live cells.

ELISA Test (Test 1a)

The anti-inflammatory effect of DOLASIX was studied via an ELISA test (Enzyme-Linked Immunosorbent Assay, Biolegend, Inc.), by quantifying the production of pro-inflammatory cytokines in the culture medium following stimulation with IL-1β and treatment with DOLASIX and with the various controls. In the "sandwich" ELISA test, a 96-well plate is covered with a monoclonal antibody specific for a given cytokine. The standards and samples are added to the wells and the cytokine of interest bonds the uptake antibody immobilized to the bottom of the well. Next, an anti-cytokine biotinylated antibody is added to the wells so that an antibody-antigen-antibody "sandwich" is formed. Horseradish peroxidase combined with streptavidin is then added, followed by a solution of tetramethylbenzidene (TMB), which, by reacting with the peroxide, produces a blue-coloured compound, the intensity of which colour is proportional to the amount of cytokine present. The addition of a sulfuric acid solution changes the colour of the solution from blue to yellow, blocking the development of the colour and allowing accurate reading of the absorbance of the samples at 450 nm.

For the purposes of the treatment, the medium was harvested and stored at −80° C. until the time of use for the test. The cells were used to measure the total protein content in the various samples. The concentrations of cytokines released into the culture medium were then expressed as pg of cytokine/mg of total protein of the sample. In this way, any differences in cytokine concentration in the medium due to a different amount of cells in the samples were eliminated.

Nuclear Translocation of NF-kB (Test 1b)

The chondrocytes were seeded onto 13 mm glass slides and, once they had reached confluence, were incubated overnight with the various treatments. The cells were fixed with 4% paraformaldehyde in PBS (15 min), permeabilized with a 0.2% solution of Triton X-100 in PBS (10 min) and the nonspecific sites for bonding with the primary antibody were blocked with a 2% solution of BSA in PBS (1 hour at room temperature). Incubation with the anti-NF-kB p65 antibody (Biolegend Inc.) diluted to 1:200 was performed in the same blocking solution (overnight at 4° C.), followed by incubation with the anti-rabbit secondary antibody coupled to the fluorophore Alexa488, diluted to 1:200 in the blocking solution. The DNA was labelled with DAPI to identify the nuclei and the glass slides were mounted with Prolong Gold (Life Technologies).

Images of the samples thus prepared were acquired on a confocal microscope (TCS SPE UV, Leica Microsystems) and were analysed with the software ImageJ v1.47h (http://imagej.nih.gov/ij) for the quantification of the nuclear translocation of NF-kB (Noursadeghi M et al., Journal of Immunological Methods, 2008, vol. 329, pages 194-200). At least 10 images relative to the nuclear signal (DAPI) and to the signal for NF-kB (Alexa488) were acquired for each sample with the 40× objective lens (ACS APO, NA 1.15, Leica Microsystems). Binary images of the signals for NF-kB and DAPI were created for each field using a threshold set at 15. The mask relative to the DAPI signal was used to define the nuclear ROIs (regions of interest). The nuclear mask was then subtracted from the binary image of NF-kB to define the cytoplasmic ROIs. These masks were then applied to the original NF-kB signals to calculate the fluorescence intensity in the nucleus and in the cytoplasm from the histograms of the intensities created with ImageJ. The mean fluorescence intensity ratio between the nucleus and the cytoplasm was then calculated for each sample.

Statistical Analysis

The quantitative data relating to the various tests were expressed as the mean±standard error. The one-way ANOVA statistical test (comparison between more than two groups) or the unpaired T test (comparison between two groups) were used to reveal statistically significant differences between the various samples.

Results

Identification Doses and Treatment Times (Test 0)

The human chondrocytes were incubated overnight with successive dilutions of DOLASIX, starting from the composition having as reference a SAMe concentration of 500 μM. To exclude a possible toxic effect attributable to the chosen incubation protocol, the cell vitality was quantified by means of an MTT test. The data obtained are collated in FIG. 1.

Figure 1:
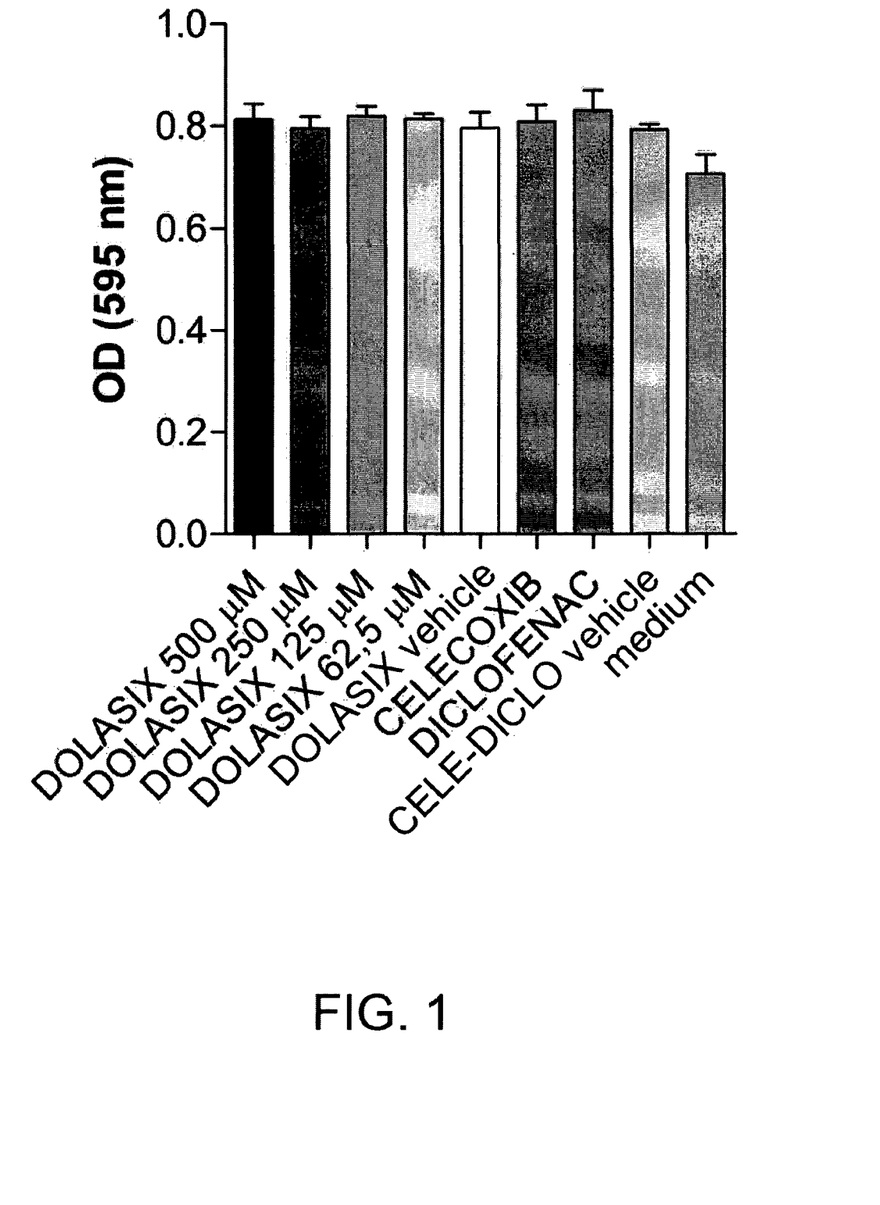
FIG. 1 shows the results of the MTT test on chondrocytes incubated with DOLASIX. The absorbance at 595 nm was measured in the various wells incubated for 16 hours with the indicated compounds at the indicated concentrations. Each bar represents the average of at least four different wells (***=p<0.001)

None of the four concentrations of DOLASIX tested proved to be toxic to the chondrocytes, and likewise for the incubation with the positive controls celecoxib (10 μM) and diclofenac (100 μM) or with the vehicles. The following tests were performed with the three highest concentrations of DOLASIX (relative to the concentration of SAMe in the final compound, of 500, 250, 125 μM).

Anti-Inflammatory Activity in Primary Human Chondrocytes (Test 1)

The anti-inflammatory activity of DOLASIX was studied via two different experimental approaches: on the one hand, the possible inhibition of the production of pro-inflammatory cytokines was quantified by means of an ELISA test (Test 1a), and, on the other hand, the possible inhibition of the nuclear translocation of NFkB was quantified by means of fluorescence immunolabelling and image acquisition using a confocal microscope (Test 1b).

ELISA Test (Test 1a)

Release into the culture medium of the pro-inflammatory cytokines TNFα, IL-6 and IL-8 by the human chondrocytes was evaluated both in the absence and in the presence of stimulation with IL-1β for 16 hours. The data obtained for TNFα are collated in FIG. 2.

Figure 2:
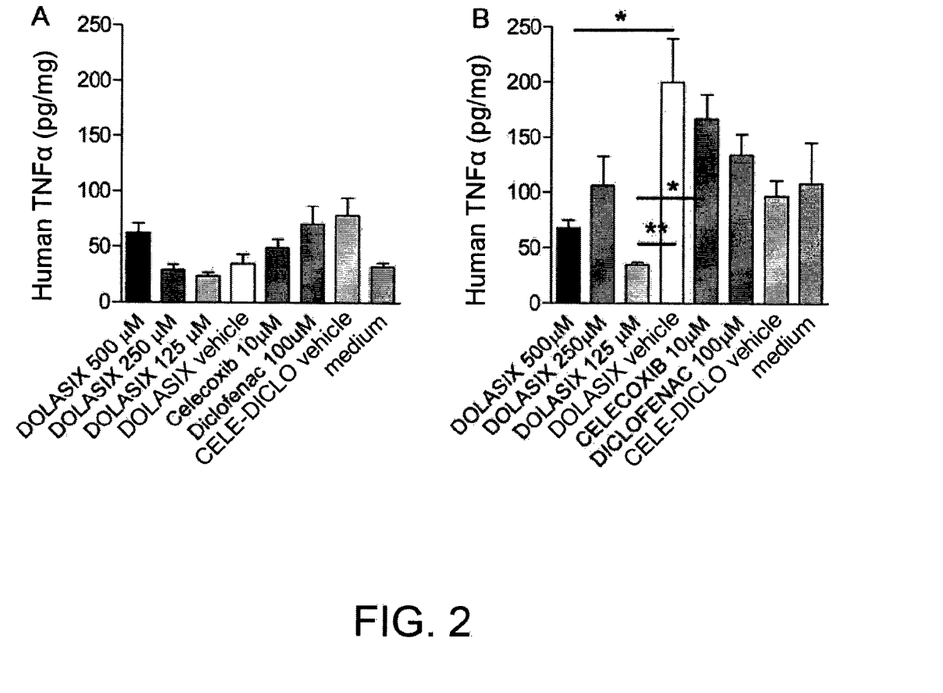
FIG. 2 shows the results of the quantification of TNFα in the culture medium of chondrocytes after pre-incubation with DOLASIX and the various controls in the absence of an inflammatory stimulus (A) or following stimulation with IL-1β 10 ng/ml for 16 hours (B). (*=p<0.05;**=p<0.01)

In the absence of an inflammatory stimulus, the production of TNFα was very low and was not substantially stimulated by incubation of the cells with IL-1β. The statistical analysis (one-way ANOVA) however revealed an inhibitory effect on the production of TNFα by DOLASIX 500 and DOLASIX 125 µM relative to incubation of the cells with the vehicle alone. Incubation both with celecoxib 10 µM and with diclofenac 100 µM in the culture medium showed no effect.

Figure 3:
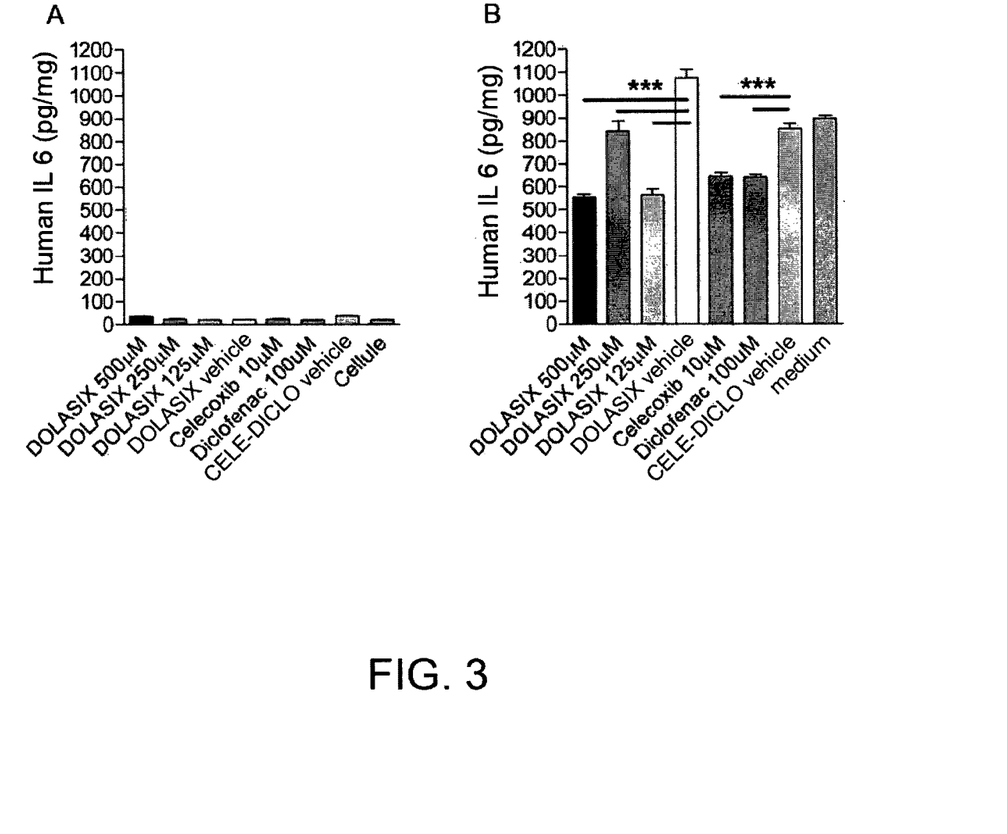
FIG. 3 shows the results of the quantification of IL-6 in the culture medium of differentiated THP-1 monocytes after pre-incubation with DOLASIX and the various controls in the absence of an inflammatory stimulus (A) or following stimulation with IL-1β10 ng/ml for 16 hours (B). ***=p<0.001.

The data relating to quantification of the release of IL-6 are collated in FIG. 3. In this case, as for the release of IL-8, the production of IL-6 in chondrocytes stimulated with IL-1β was so large that, to avoid saturation of the signal, the samples of medium were diluted to 1:1000 before being processed in the ELISA test.

All the concentrations of DOLASIX tested showed a statistically significant inhibitory effect, relative to incubation with the vehicle alone, on the production and release of IL-6 by the stimulated chondrocytes. The inhibitory effect on cytokine release of DOLASIX 500 µM and 125 µM was comparable to that shown by celecoxib or diclofenac (n.s.).

Figure 4:
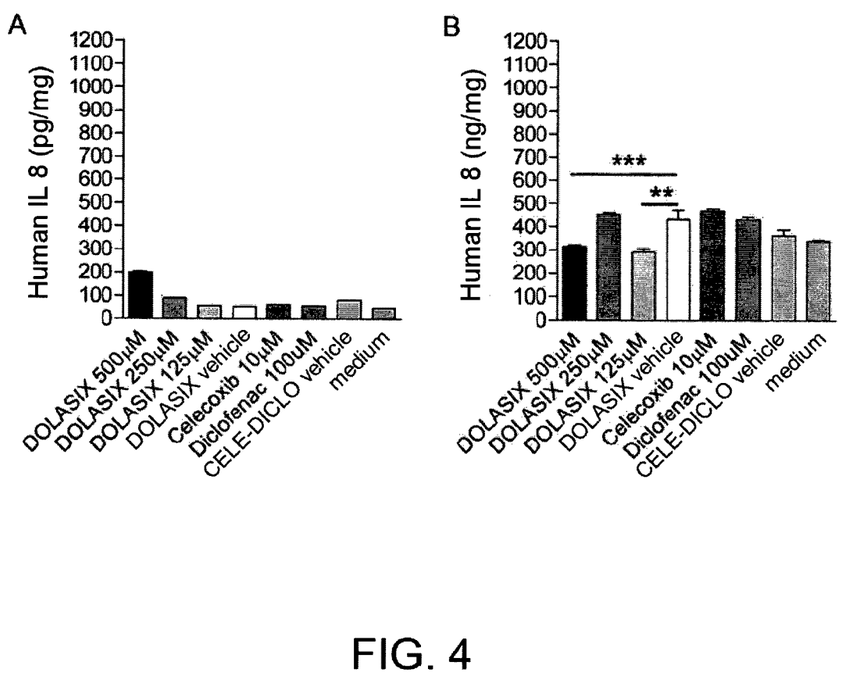
FIG. 4 shows the results of the quantification of IL-8 in the culture medium of human chondrocytes after pre-incubation with DOLASIX and the various controls in the absence of an inflammatory stimulus (A) or following stimulation with IL-1β 10 ng/ml for 16 hours (B). (*=p<0.001; =p<0.01)

The data relating to the quantification of the release of IL-8 are collated in FIG. 4.

As for IL-6, the release of IL-8 by the stimulated chondrocytes was so large that the samples of medium were diluted to 1:1000 before being processed in the ELISA test to avoid saturation of the signal. The different scale (ng/mg) on the y-axis in FIG. 4B relative to the scale in FIG. 4A (pg/mg) may be noted. Incubation both with DOLASIX 500 µM and with DOLASIX 125 µM showed a statistically significant reduction in IL-8 production by the stimulated chondrocytes (FIG. 3B) relative to incubation with the vehicle alone. DOLASIX 500 µM and DOLASIX 125 µM were more effective than either celecoxib or diclofenac.

Nuclear Translocation of NF-kB (Test 1b)

Figure 5:
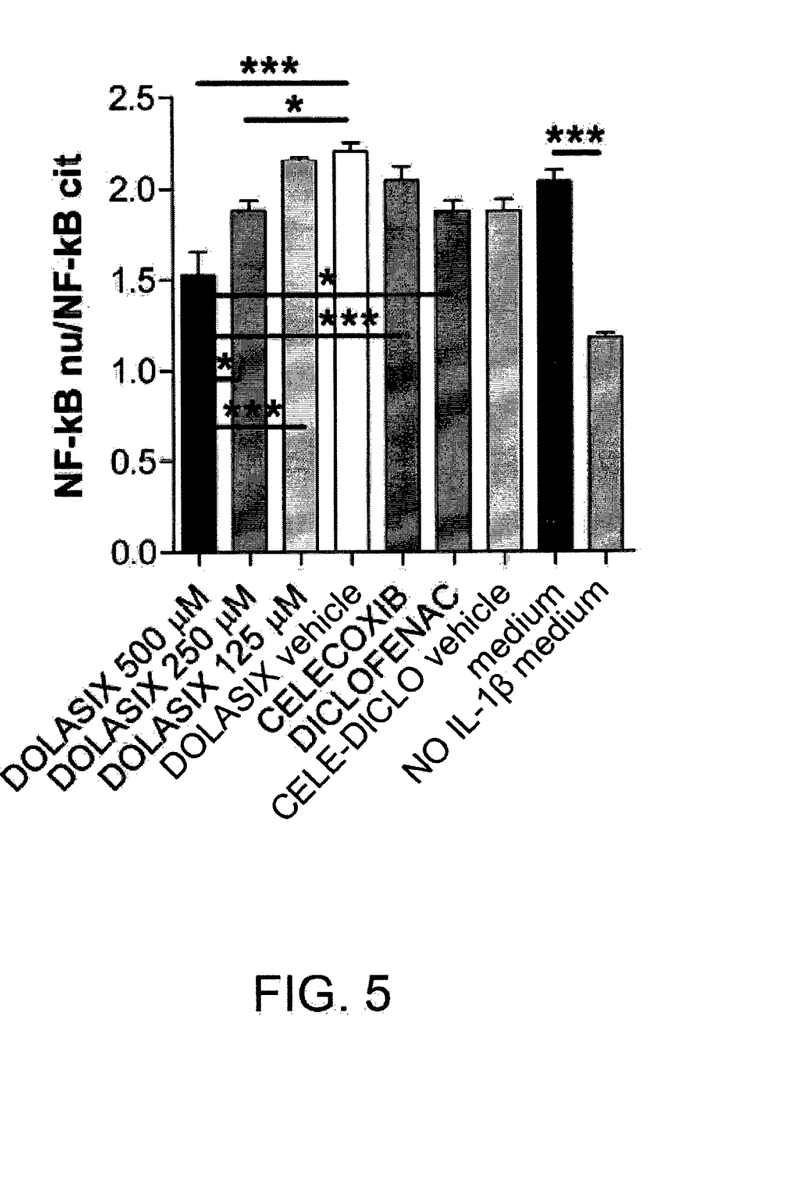
FIG. 5 shows the results of the quantification of nuclear translocation of NF-kB. As described in the experimental section, the fluorescence ratio in the nucleus and in the cytoplasm was calculated to reveal the translocation of NF-kB.

Quantification of the nuclear translocation of NF-kB following inflammatory stimulation with IL-1β and in the presence or absence of preincubation with DOLASIX, with diclofenac, celecoxib or with the respective negative controls revealed a clearly antagonizing role of DOLASIX on the translocation of NF-kB to the nucleus (FIG. 5).

All the samples, except the one named "NO IL-1β medium", were stimulated with IL-1β for about 20 hours before being processed for the immunolabelling of NF-kB. As expected, in the non-stimulated cells, the presence of NF-kB in the nucleus was significantly less than that in the cells stimulated with IL-1β. While incubation with diclofenac and celecoxib had no significant effect on the translocation of NF-kB to the nucleus in the presence of the inflammatory stimulus, preincubation with DOLASIX inhibited the translocation of NF-kB in a concentration-dependent manner, only the highest two concentrations (500 and 250 µM) being effective.

CONCLUSIONS

In conclusion, DOLASIX demonstrated effective anti-inflammatory properties both in reducing the production of pro-inflammatory cytokines and in inhibiting the nuclear translocation of the transcription factor NF-kB following stimulation with IL-1β in the primary human chondrocyte cell model used for this study.

The invention claimed is:

1. A pharmaceutical composition or dietary supplement, in a dosage form, comprising a combination of:
   i) from 1 to 4 g of methylsulfonylmethane,
   ii) from 100 to 300 mg of unsaponifiables of soybean and avocado with a phytosterol titre of at least 30%, and
   iii) from 50 to 200 mg of S-adenosyl-L-methionine,
   wherein the combination is formulated for use in the treatment of arthropathies and osteoarthritis.

2. The pharmaceutical composition or dietary supplement according to claim 1, wherein S-adenosyl-L-methionine is in the form of S-adenosyl-L-methionine sulfate p-toluenesulfonate.

3. The pharmaceutical composition or dietary supplement according to claim 1, comprising about 2.5 g of methylsulfonylmethane, about 150 mg of unsaponifiables of soybean and avocado and about 100 mg of S-adenosyl-L-methionine.

4. The pharmaceutical composition or dietary supplement according to claim 1, which is in an oral dosage form.

5. The pharmaceutical composition or dietary supplement according to claim 1, comprising one or more further active ingredients selected from vitamin C, copper and manganese.

6. The pharmaceutical composition or dietary supplement according to claim 5, wherein copper is in the form of copper bisglycinate and manganese is in the form of manganese bisglycinate.

7. The composition according to claim 1, further comprising pharmaceutically acceptable excipients and/or binders and/or vehicles.

8. A method of treating arthropathies and osteoarthritis comprising:
   administering an effective amount of a pharmaceutical composition or dietary supplement comprising a combination of:
   i) from 1 to 4 g of methylsulfonylmethane,
   ii) from 100 to 300 mg of unsaponifiables of soybean and avocado with a phytosterol titre of at least 30%, and
   iii) from 50 to 200 mg of S-adenosyl-L-methionine to a patient suffering from arthropathies or osteoarthritis.

9. The method according to claim 8, wherein S-adenosyl-L-methionine is in the form of S-adenosyl-L-methionine sulfate p-toluenesulfonate.

10. The method according to claim 8, wherein said pharmaceutical composition or dietary supplement is in a dosage form comprising about 2.5 g of methylsulfonylmethane, about 150 mg of unsaponifiables of soybean and avocado and about 100 mg of S-adenosyl-L-methionine.

11. The method according to claim 8, wherein said pharmaceutical composition or dietary supplement is in an oral dosage form.

12. The method according to claim 8, wherein said pharmaceutical composition or dietary supplement comprises one or more further active ingredients selected from vitamin C, copper and manganese.

13. The method according to claim 12, wherein copper is in the form of copper bisglycinate and manganese is in the form of manganese bisglycinate.

14. The method according to claim 8, wherein said pharmaceutical composition or dietary supplement further comprises pharmaceutically acceptable excipients and/or binders and/or vehicles.

* * * * *